(12) United States Patent
Jin et al.

(10) Patent No.: US 9,246,104 B2
(45) Date of Patent: Jan. 26, 2016

(54) FULLERENE DERIVATIVE, METHOD OF MANUFACTURING FULLERENE DERIVATIVE AND SOLAR CELL

(71) Applicants: SHOWA DENKO K.K., Tokyo (JP); Tohoku University, Miyagi (JP)

(72) Inventors: Tienan Jin, Miyagi (JP); Weili Si, Miyagi (JP); Yoshinori Yamamoto, Miyagi (JP); Takeshi Igarashi, Tokyo (JP)

(73) Assignees: SHOWA DENKO K.K., Tokyo (JP); Tohoku University, Miyagi (JP)

( * ) Notice: Subject to any disclaimer, the term of this patent is extended or adjusted under 35 U.S.C. 154(b) by 148 days.

(21) Appl. No.: 14/036,189

(22) Filed: Sep. 25, 2013

(65) Prior Publication Data

US 2015/0083223 A1    Mar. 26, 2015

(51) Int. Cl.
H01L 51/00    (2006.01)

(52) U.S. Cl.
CPC .................................. *H01L 51/0047* (2013.01)

(58) Field of Classification Search
CPC .................................................. H01L 51/0047
USPC ......................................................... 136/263
See application file for complete search history.

(56) References Cited

U.S. PATENT DOCUMENTS

2010/0317767 A1* 12/2010 Tanaka et al. ................. 523/400
2011/0313189 A1  12/2011 Varotto et al.

FOREIGN PATENT DOCUMENTS

| CA | 2687557 | 12/2008 |
|---|---|---|
| JP | 2002-088075 | 3/2002 |
| WO | WO2009/002203 | 12/2008 |

OTHER PUBLICATIONS

Chang-Zhi Li et al., Functional fullerenes for organic photovoltaics, J. Mater. Chem., 2012, 22, pp. 4161-4177.
Ying Zhang et al., A Scalable Synthesis of Methano[60]fullerene and Congeners by the Oxidative Cyclopropanation Reaction of Silylmothylfullerene, J. Am. Chem. Soc. 2011, 133, pp. 8086-8089.
Alessandro Varotto at al., 1,4-Fullerene Derivatives: Tuning the Properties of the Electron Transporting Layer in Bulk-Heterojunction Solar Cells, Angew. Chem. Int. Ed. 2011, 50, pp. 5166-5169.
Shunichi Fukuzumi et al., Formation of C60 Adducts with Two Different Alkyl Groups via Combination of Electron Transfer and SN2 Reactions, J. Am. Chem. Soc., vol. 120, No. 36, 1998, pp. 9220-9227.
Yutaka Matsuo et al., Regioselective Synthesis of 1,4-Di(organo)[60]fullerenes through DMF-assisted Monoaddition of Silylmethyl Grignard Reagents and Subsequent Alkylation Reaction, J. Am. Chem. Soc. 2008, 130, pp. 15429-15436.
Yasujino Murata et al., Generation of Fullerenyl Cation (EtO)2P+(OH)CH2-C60 + from RC60-H and from RC60-C60R (R= CH2P(O)(OEt)2), J. Am. Chem. Soc. vol. 126, No. 29, 2004, pp. 19674-8875.
Shirong Lu at al., Highly Efficient Cu(OAc)2-Catalyzed Dimerization of Monofunctionalized Hydrofullerenes Leading to Single-Bonded [60]Fullerene Dimers, Angew. Chem. Int. Ed. 2012, 51, pp. 802-806.
Shirong Lu at al., NaOH-Catalyzed Dimerization of Monofunctionalized Hydrofullerenes: Transition-Metal-Free, General, and Efficient Synthesis of Single-Bonded [60]Fullerene Dimers, Org. Lett., vol. 14, No. 13, 2012, pp. 3466-3469.
Andreas Hirsch et al., Globe-trotting Hydrogens on the Surface of the Fullerene Compound C60H6(N(CH2CH2)2O)6, Angew. Chem. Int. Ed. Engl. 30, No. 10, 1991, pp. 1309-1310.
Shirong Lu et al., Cobalt-Catalyzed Hydroalkylation of [60]Fullerene with Active Alkyl Bromides: Selective Synthesis of Monoalkylated Fullerenes, J. Am, Chem. Soc. 2011, 133, pp. 12842-12848.
Ying Zhang et al., Regiocontrolled Synthesis of 1,2-Di(organo)fullerenes via Copper-Assisted 1,4-Aryl Migration from Silicon to Carbon, Org. Lett., vol. 13, No. 22, 2011, pp. 6058-6061.

* cited by examiner

*Primary Examiner* — Taofiq A Solola
(74) *Attorney, Agent, or Firm* — IPUSA, PLLC

(57) ABSTRACT

A fullerene derivative represented by the following formula (1):

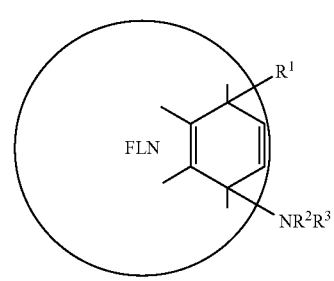

(1)

wherein "FLN" represents a fullerene core, $R^1$ represents an optionally substituted $C_1$-$C_{24}$ alkyl group or an optionally substituted $C_7$-$C_{24}$ aralkyl group, $R^2$ and $R^3$ independently represent a hydrogen atom or an optionally substituted $C_1$-$C_{24}$ hydrocarbon group but excluding a case where both of $R^2$ and $R^3$ are hydrogen atoms, and $R^2$ and $R^3$ may combine together to form a ring.

11 Claims, 4 Drawing Sheets

FULLERENE DERIVATIVE, METHOD OF MANUFACTURING FULLERENE DERIVATIVE AND SOLAR CELL

BACKGROUND OF THE INVENTION

1. Field of the Invention

The present invention relates to a fullerene derivative, a method of manufacturing a fullerene derivative and a solar cell.

2. Description of the Related Art

Fullerenes, prepared first in 1985, are a third carbon allotrope in which 60 or more carbon atoms are bonded in a spherical shape. Fullerenes, typically as $C_{60}$, $C_{70}$, $C_{76}$, $C_{78}$, $C_{82}$, $C_{84}$ or the like, have been marked as new functional materials for electronic components, drugs, cosmetics or the like because of their specific molecular shapes.

For methods of manufacturing fullerenes, arc discharging, resistance heating, laser vaporization, a combustion method, thermal decomposition or the like are known. By any methods, soot including fullerenes are generated. The fullerenes capable of being dissolved in organic solvent such as $C_{60}$, $C_{70}$, $C_{76}$, $C_{78}$, $C_{82}$, $C_{84}$ or the like are obtained by extracting the soot by the organic solvent. Further, by chemically-modifying these fullerenes to obtain fullerene derivatives, it is possible to improve solubility of the fullerene derivatives to organic solvent or water.

Conventionally, fullerene derivatives modified with a substituent group such as a hydrocarbon group or the like have been reported. Among these, fullerene derivatives modified with an amino group are very interesting materials expected to be applicable for various materials because they have a high solubility to organic solvent or the like and it is possible to directly control an electron accepting function of the fullerene.

Patent Document 1 disclose a method of manufacturing fullerene derivatives modified with amino groups by adding amine compounds to a fullerene. However, according to the method disclosed in non Patent Document 1, a fullerene derivative added with six amino groups and six hydrogen atoms is obtained. Further, according to the method disclosed in Patent Document 1, only a fullerene derivative modified with four amino groups and one epoxy group, and a fullerene derivative modified with five amino groups and one hydroxyl group are obtained.

It has been difficult to selectively add one amino group to a fullerene derivative. When fullerene derivatives are used for diodes for organic thin film solar cells or the like, the number of substituent groups may be two in order to retain original characteristics of fullerenes such as an electron accepting function or an electron transporting function. Further, it is desirable to introduce not only an amino group but also another substituent group to fullerenes in order to precisely control the electron accepting function of the fullerenes.

Patent Document 2 discloses a method of manufacturing a fullerene derivative including a phenyl group and a phenylamino group by applying aniline to fullerenol as a source material. However, the obtained fullerene derivative includes an aryl group such as a phenyl group, a tolyl group or the like. Generally, the fullerene derivative substituted by the aryl group has a low solubility. Thus, it was difficult to form a thin film of a fullerene derivative using a solution process such as a printing method or the like for an organic thin film solar cell or the like.

Patent Document 3 discloses a method of manufacturing a fullerene derivative including an alkyl group and an amino group. However, the alkyl group and the amino group are limited to be provided at 1,2 position and it was impossible to manufacture a fullerene derivative in which the alkyl group and the amino group are provided at 1,4 position. It means that a degree of freedom in a molecular design was limited. As will be explained later, 1,4-difunctionalized fullerene derivatives possessing two identical or unsymmetrical functional groups on 1,4-position of a fullerene core such as $C_{60}$ or the like are expected to offer various functional properties.

DOCUMENTS

Patent Document 1: Japanese Laid-open Patent Publication No. 2002-88075
Patent Document 2: US2011/0313189
Patent Document 3: WO2009/002203 (CA2687557)

SUMMARY OF THE INVENTION

The present invention is made in light of the above problems, and provides a 1,4-fullerene derivative having a monoamino addend synthesized under a mild reaction condition.

According to an embodiment, there is provided a fullerene derivative represented by the following formula (1):

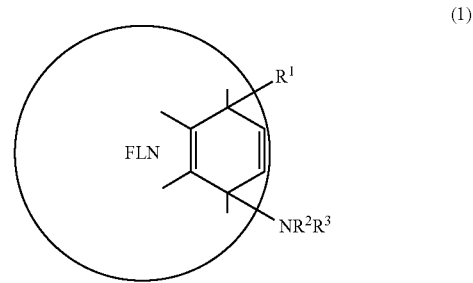

(1)

wherein "FLN" represents a fullerene core, $R^1$ represents an optionally substituted $C_1$-$C_{24}$ alkyl group or an optionally substituted $C_7$-$C_{24}$ aralkyl group, $R^2$ and $R^3$ independently represent a hydrogen atom or an optionally substituted $C_1$-$C_{24}$ hydrocarbon group but excluding a case where both of $R^2$ and $R^3$ are hydrogen atoms, and $R^2$ and $R^3$ may combine together to form a ring.

According to another embodiment, there is provided a method of manufacturing a fullerene derivative represented by the following formula (1), including reacting a fullerene derivative represented by the following formula (3) and an amine compound represented by the following formula (4) in the presence of a Cu-based catalyst and oxygen:

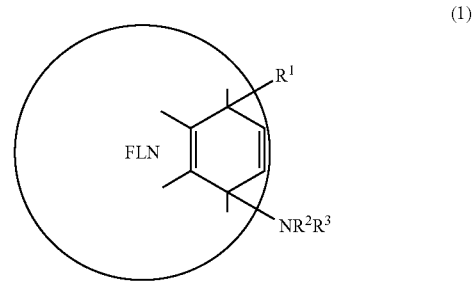

(1)

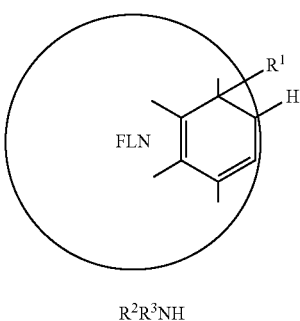

(3)

(4)

R²R³NH wherein "FLN" represents a fullerene core, $R^1$ represents an optionally substituted $C_1$-$C_{24}$ alkyl group or an optionally substituted $C_7$-$C_{24}$ aralkyl group, $R^2$ and $R^3$ independently represent a hydrogen atom or an optionally substituted $C_1$-$C_{24}$ hydrocarbon group but excluding a case where both of $R^2$ and $R^3$ are hydrogen atoms, and $R^2$ and $R^3$ may combine together to form a ring.

According to another embodiment, there is provided a solar cell including a substrate; a first electrode; an active layer; and a second electrode, stacked in this order, wherein the active layer includes an electron donor compound, and an electron acceptor compound including a fullerene derivative represented by the following formula (1):

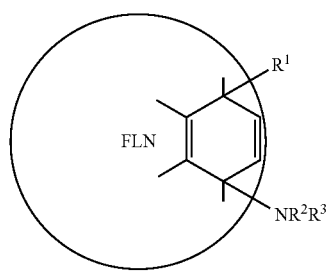

(1)

wherein "FLN" represents a fullerene core, $R^1$ represents an optionally substituted $C_1$-$C_{24}$ alkyl group or an optionally substituted $C_7$-$C_{24}$ aralkyl group, $R^2$ and $R^3$ independently represent a hydrogen atom or an optionally substituted $C_1$-$C_{24}$ hydrocarbon group but excluding a case where both of $R^2$ and $R^3$ are hydrogen atoms, and $R^2$ and $R^3$ may combine together to form a ring.

Note that also arbitrary combinations of the above-described elements, and any changes of expressions in the present invention, made among methods, devices and so forth, are valid as embodiments of the present invention.

BRIEF DESCRIPTION OF THE DRAWINGS

Other objects, features and advantages of the present invention will become more apparent from the following detailed description when read in conjunction with the accompanying drawings.

DETAILED DESCRIPTION OF THE PREFERRED EMBODIMENTS

Figure 1:
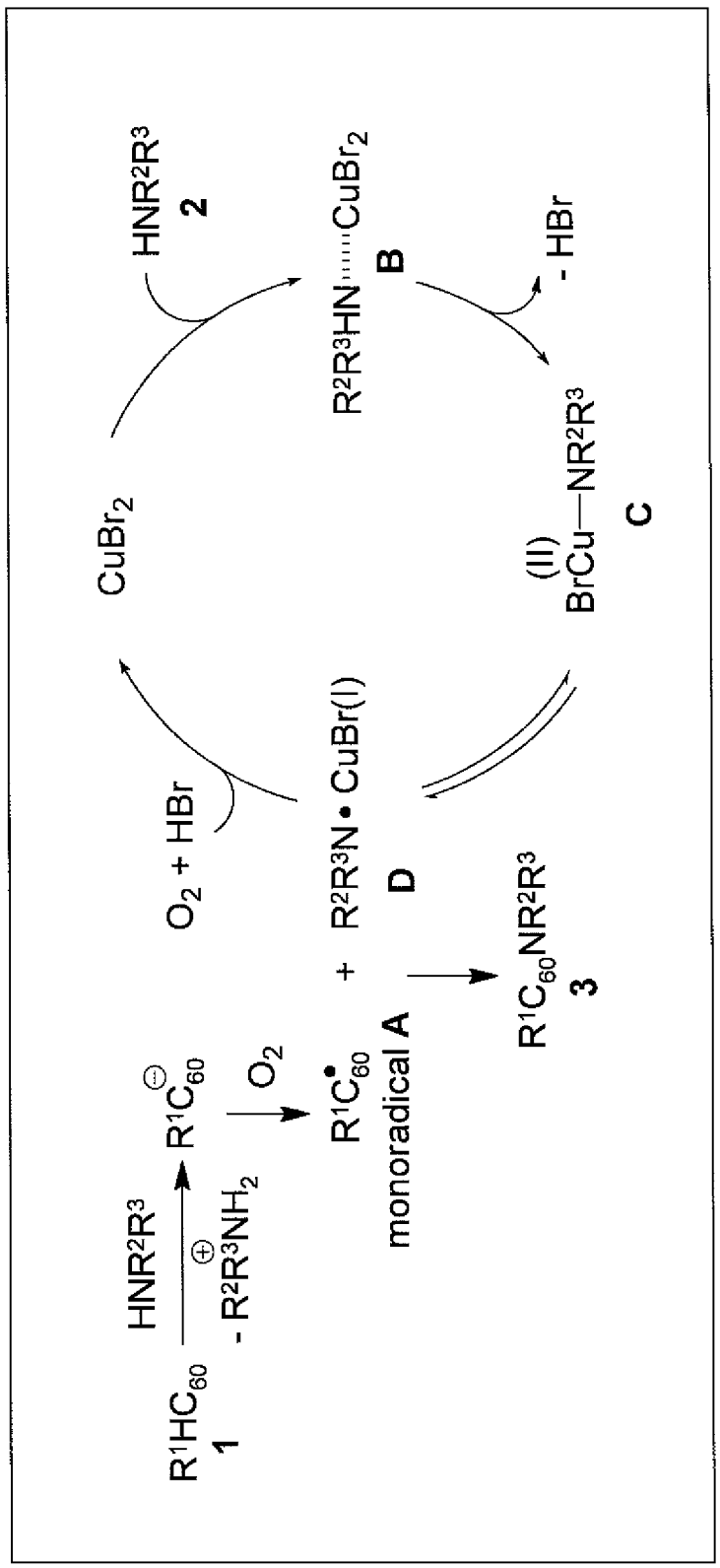
FIG. 1 is a view illustrating an example of a scheme of the reaction mechanism of the embodiment.

The invention will be described herein with reference to illustrative embodiments. Those skilled in the art will recognize that many alternative embodiments can be accomplished using the teachings of the present invention and that the invention is not limited to the embodiments illustrated for explanatory purposes.

It is to be noted that, in the explanation of the drawings, the same components are given the same reference numerals, and explanations are not repeated.

1,4-Difunctionalized fullerene derivatives possessing two identical or unsymmetrical functional groups on 1,4-position of a fullerene core such as $C_{60}$ or the like are expected to offer a tunable energy level, solubility, and packing structure through wide structural variations (reference (1)). In addition, the 1,4-difunctional fullerene derivatives may exhibit higher absorption extinction coefficient in the visible region, that makes them attractive as n-type materials for high performance organic photovoltaics.

However, despite the interesting properties of 1,4-difunctionalized fullerene derivatives, only a limited number of synthetic methods have been developed (references (2a) to (4)).

Matsuo et. al. reported an efficient method for the synthesis of 1,4-dialkylfullerenes through the deprotonation of mono-silylmethyl hydrofullerene followed by alkylation with alkyl halides (reference (3b)). The reaction of fullerene dianion with alkyl halides is an alternative methodology for the synthesis of 1,4-dialkylfullerenes (reference (3a)). 1,4-Diarylfullerenes are also reported to be synthesized by the acids-assisted nucleophilic substitution of fullerenyl cation (reference (4)).

Although 1,4-bisadducts with an amine addend directly substituted to a fullerene core such as $C_{60}$ or the like are expected to exhibit the various functional properties compared to those dialkyl and diaryl 1,4-bisadducts, only one example of monoamine functionalized 1,4-bisadducts has been reported (reference (2b)). Varotto et. al. synthesized aniline substituted 1,4-bisadducts by the acid-mediated reaction of fullerenol with aniline, which showed a lower lowest unoccupied molecular orbital (LUMO) energy than that of diaryl 1,4-bisadducts.

Recently, it has been reported that fullerene mono radical can be readily formed from mono-functionalized hydrofullerenes catalyzed by $Cu(OAc)_2$ oxidant or NaOH base under air atmosphere, affording single-bonded fullerene dimers in high yields (references (5a) and (5b)). During the investigation of dimerization conditions by a combination of Cu-based catalyst and amine base, the present inventors surprisingly found that the monoamine substituted 1,4-bisadducts were formed as the major product instead of the fullerene dimer.

Herein, the present inventors report a novel C—H amination of monosubstituted hydrofullerenes with various amines to afford a new series of monoamine functionalized 1,4-bisadducts in good to high yields.

It is noted that, while the addition of amines to $C_{60}$ resulted in formation of multiadducts (reference (6)), a method of manufacturing a fullerene derivative of the embodiment affords a monoamine functionalized 1,4-bisadduct fullerene derivative.

According to the present embodiment, a fullerene derivative including a fullerene core; and a first functional group represented by $R^1$ and a second functional group represented by $NR^2R^3$ provided on 1,4-position of the fullerene core is provided. Specifically, according to the present embodiment, a fullerene derivative 3', which is a monoamine functionalized 1,4-bisadduct fullerene derivative, represented by the following formula (1) is provided by a reaction represented by the following formula (2).

(1)

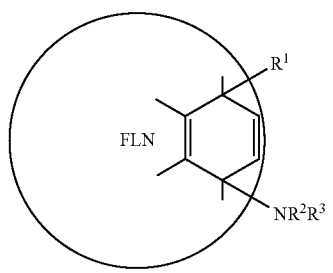

Here, $R^1$ represents an optionally substituted $C_1$-$C_{24}$ alkyl group or an optionally substituted $C_7$-$C_{24}$ aralkyl group.

The kind of a substituent group that is substituted by a hydrogen atom on the alkyl group or the aralkyl group is not limited as long as that does not largely influence on the properties of the fullerene derivative of the embodiment. Specifically, the substituent group may be a $C_1$-$C_{10}$ hydrocarbon group (for example, methyl, ethyl, propyl, butyl, phenyl, naphthyl, indenyl, tolyl, xylyl, benzyl or the like), a $C_1$-$C_{10}$ alkoxy group (for example, a methoxy group, an ethoxy group, a propoxy group, a butoxy group, a benzyloxy group or the like), a $C_6$-$C_{12}$ aryloxy group (for example, phenyloxy, naphthyloxy, biphenyloxy or the like), a $C_1$-$C_{10}$ acyloxy group (for example, an acetoxy group or the like), an aldehyde group, a $C_1$-$C_{10}$ oxycarbonyl group (for example, a methoxycarbonyl group, a hexyloxycarbonyl group or the like), a $C_1$-$C_{10}$ acyl group (for example, acetyl group or the like), a nitro group, an amino group (an amino group, a methylamino group, a dimethylamino group, a methylphenylamino group, a phenylamino group or the like), an amide group, a nitrile group, a silyl group (for example, a trimethylsilyl group, a dimethylphenylsilyl group or the like), a phosphine group (for example, a tributylphosphine group, a triphenylphosphine group or the like), a halogen atom (for example, fluorine, chlorine, bromine, iodine or the like), or the like.

Further, two or more of the substituent groups may be provided on $R^1$ (the alkyl group or the aralkyl group). For example, two to four of the substituent groups may be provided on substitutable positions of the alkyl group or the aralkyl group. When two or more of the substituent groups are provided, the substituent groups may be the same or different.

Specifically, $R^1$ may be a benzyl group without a substituent group, or with a substituent group(s) on a position(s) of the benzene ring selected from a group including a $C_1$-$C_{10}$ hydrocarbon group (for example, methyl, ethyl, propyl, butyl, phenyl, naphthyl, indenyl, tolyl, xylyl, benzyl or the like), a $C_1$-$C_{10}$ alkoxy group (for example, a methoxy group, an ethoxy group, a propoxy group, a butoxy group, a benzyloxy group or the like) and a $C_1$-$C_{10}$ oxycarbonyl group (for example, a methoxycarbonyl group, a hexyloxycarbonyl group or the like). In particular, $R^1$ may be a benzyl group without a substituent group, or with a substituent group(s) on a position(s) of the benzene ring selected from a group including a methoxy group, and a methoxycarbonyl group.

For example, $R^1$ is a benzyl group having at least one substituent group on a position of the benzene ring selected from a group including a methoxycarbonyl group, a hexyloxycarbonyl group, a methoxy group and the like, or an alkyl group having at least one substituent group selected from a benzyloxy group and the like.

$R^2$ and $R^3$ independently represent a hydrogen atom or an optionally substituted $C_1$-$C_{24}$ hydrocarbon group but excluding a case where both of $R^2$ and $R^3$ are hydrogen atoms, and $R^2$ and $R^3$ may combine together to form a ring.

The hydrocarbon group may be, for example, an alkyl group such as a methyl group, an ethyl group, a propyl group or the like, an aromatic group such as a phenyl group, an indenyl group, a naphthyl group, an anthracenyl group, a phenanthrenyl group, a fluorenyl group, a pyrenyl group or the like, or an aralkyl group such as a benzyl group, a 2-phenylethyl group, a 1-phenylethyl group, a 3-phenylpropyl group or the like.

Further, when $R^2$ and $R^3$ combine together to form a ring, a part of the ring may be substituted by an atom such as oxygen, nitrogen, sulfur, silicon or the like, and the ring may be further condensed with another ring.

Further, the kind of a substituent group that is substituted by a hydrogen atom on the hydrocarbon group is not limited as long as that does not largely influence on the properties of the fullerene derivative of the embodiment. Specifically, the substituent group may be a $C_1$-$C_{10}$ hydrocarbon group (for example, methyl, ethyl, propyl, butyl, phenyl, naphthyl, indenyl, tolyl, xylyl, benzyl or the like), a $C_1$-$C_{10}$ alkoxy group (for example, a methoxy group, an ethoxy group, a propoxy group, a butoxy group or the like), a $C_6$-$C_{12}$ aryloxy group (for example, phenyloxy, naphthyloxy, biphenyloxy or the like), a $C_1$-$C_{10}$ acyloxy group (for example, an acetoxy group or the like), an aldehyde group, a $C_1$-$C_{10}$ oxycarbonyl group (for example, a methoxycarbonyl group, a hexyloxycarbonyl group or the like), a $C_1$-$C_{10}$ acyl group (for example, an acetyl group or the like), a nitro group, an amino group (an amino group, a methylamino group, a dimethylamino group, a methylphenylamino group, a phenylamino group or the like), an amide group, a nitrile group, a silyl group (for example, a trimethylsilyl group, a dimethylphenylsilyl group or the like), a phosphine group (for example, a tributylphosphine group, a triphenylphosphine group or the like), a halogen atom (for example, fluorine, chlorine, bromine, iodine or the like), or the like.

Further, two or more of the substituent groups may be provided on the hydrocarbon group. For example, two to four of the substituent groups may be provided on substitutable positions of the hydrocarbon group. When two or more of the substituent groups are provided, the substituent groups may be the same or different.

Specifically, $R^2R^3N—$ may be a methylamino group, an ethylamino group, a n-propylamino group, an isopropylamino group, a n-butylamino group, an isobutylamino group, a n-hexylamino group, a benzylamino group, a phenylamino group, a tolylamino group, a dimethylamino group, a diethylamino group, a di(n-propyl)amino group, a diisopropylamino group, a di(n-butyl)amino group, a diisobutylamino group, a di(n-hexyl)amino group, a dibenzylamino group, a diphenylamino group, a ditolylamino group, a methylphenylamino group, a piperidino group, a morpholino group, a thiomorpholino group, a tetrahydroisoquinolino group or the like. In particular, $R^2R^3N$— may be a morpholino group.

"FLN" represents a fullerene core. The fullerene core represented by "FLN" may be a single fullerene core selected from a group including $C_{60}$, $C_{70}$, $C_{76}$, $C_{78}$, $C_{82}$, $C_{84}$ and the like, or a mixture of two or more of fullerene cores selected from the group including $C_{60}$, $C_{70}$, $C_{76}$, $C_{78}$, $C_{82}$, $C_{84}$ and the like. Preferably, the fullerene core represented by "FLN" may be C60, C70 or a mixture thereof. More preferably, the fullerene core represented by "FLN" may be C60.

(2)

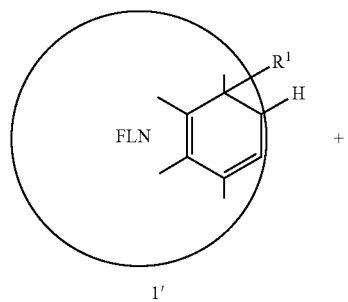

1'

$R^2R^3NH$  $\xrightarrow{\text{Catalyst}}_{O_2}$

2

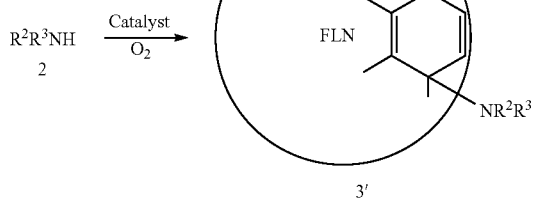

3'

In the formula (2), a source fullerene derivative 1', which is a mono-functionalized hydro-fullerene derivative, represented by the following formula (3) and an amine compound 2 represented by the following formula (4) are reacted in the presence of a catalyst and oxygen.

(3)

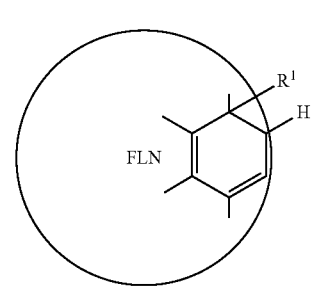

1'

(4)

$R^2R^3NH$

2

In the following, an example when the fullerene core represented by "FLN" is $C_{60}$ is explained. At this time, the above equations (1) to (3) are expressed as following equations (1A) to (3A), respectively.

(1A)

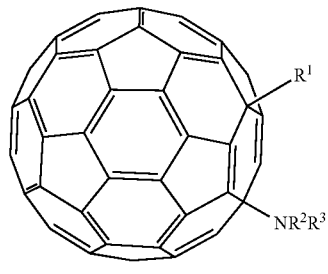

3

(2A)

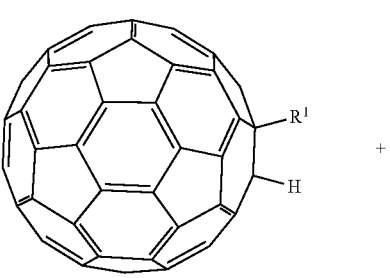

1

$R^2R^3NH$  $\xrightarrow{\text{Catalyst}}_{O_2}$

2

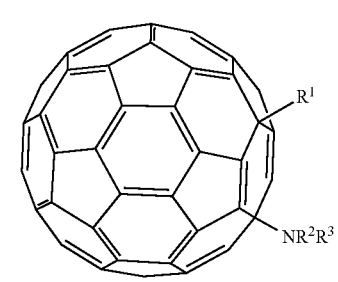

3

(3A)

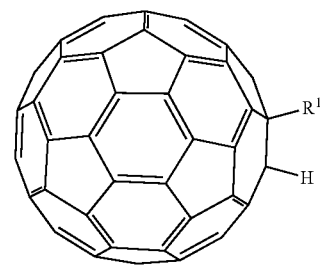

1

(Catalyst)

For the catalyst used in the reaction represented by the formula (2), a Cu-based catalyst may be used. For the Cu-based catalyst, Cu(II) species such as $CuBr_2$, $Cu(OTf)_2$, $CuCl_2$ or the like, and Cu(I) species such as $Cu_2O$, CuCl, CuBr, CuI or the like may be used. In particular, $CuBr_2$ may be used as the Cu-based catalyst.

(Solvent)

For the solvent used in the reaction represented by the formula (2), there is no limitation as long as the source fullerene derivative 1' and the amine compound 2 are soluble, however, aromatic series solvent (benzene, toluene, o-xylene, m-xylene, p-xylene, 1,3,5-trimethyl benzene, 1,2,4-trimethyl benzene, 1-methyl naphthalene, tetralin, anisole, chlorobenzene, 1,2-dichlorobenzene) or carbon disulfide are preferable because solubility of the source fullerene derivative 1' is high and productivity is also high. Among them, 1,2-dichlorobenzene is particularly preferable. Further, a mixture of two or more solvent may be used. At this time, it is preferable to add aprotic polar solvent in addition to the aromatic series solvent in order to improve reaction yield. For the aprotic polar solvent, such as acetonitrile ($CH_3CN$), acetone, tetrahydrofuran (THF), dimethylformamide (DMF), dimethylacetamide, dimethyl sulfoxide, N-methyl-2-pyrrolidone or the like may be used. In particular, DMF may be preferably used. The ratio of the aromatic series solvent and the aprotic polar solvent (aromatic series solvent: aprotic polar solvent) are not specifically limited, however, preferably, 99:1 to 20:80, and more preferably, 90:10 to 50:50.

(Source Fullerene Derivative 1)

The source fullerene derivative 1 is represented by the above described formula (3). $R^1$ may be described as above.

Figure 2:
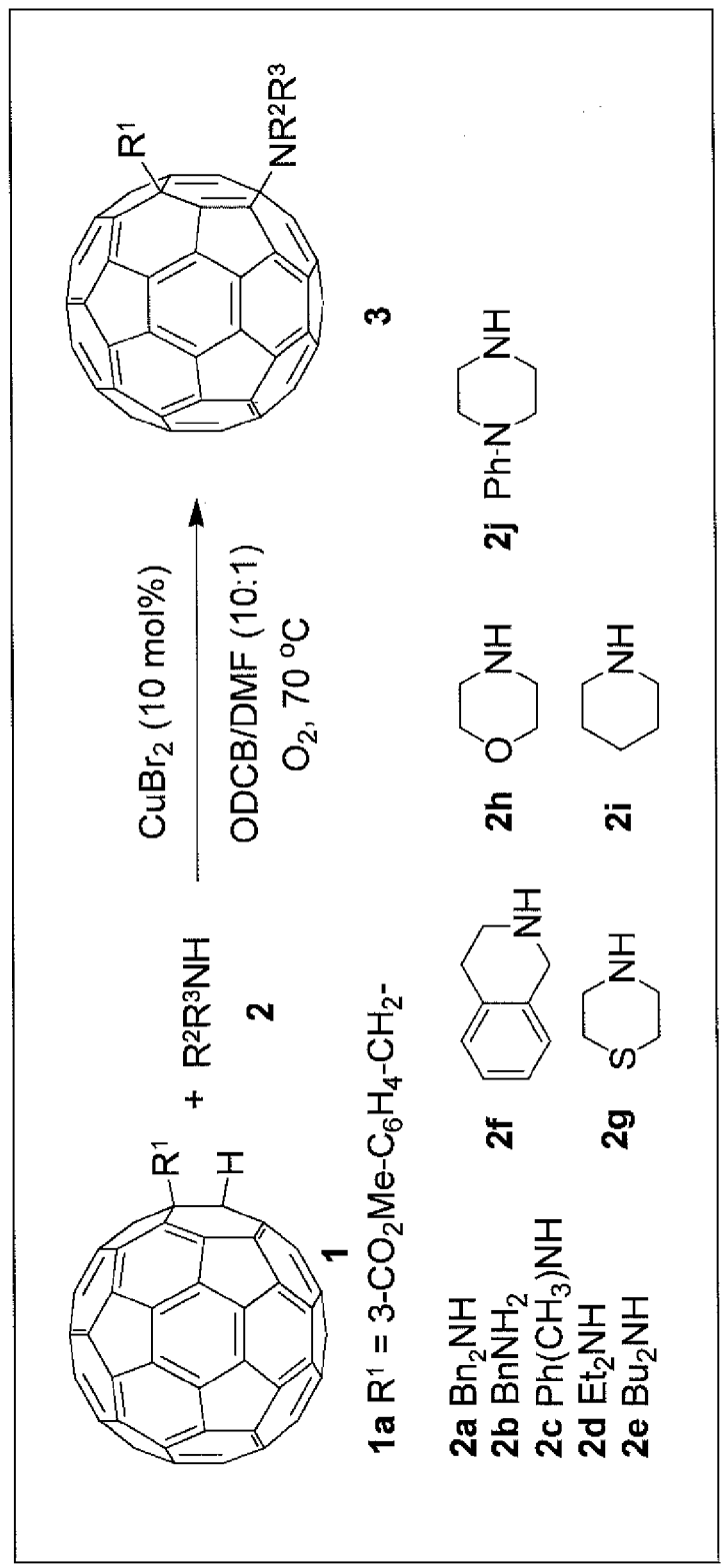
FIG. 2 is a view illustrating an example of an equation between a source fullerene derivative and an amine compound to form a fullerene derivative of the embodiment.
Figure 3:
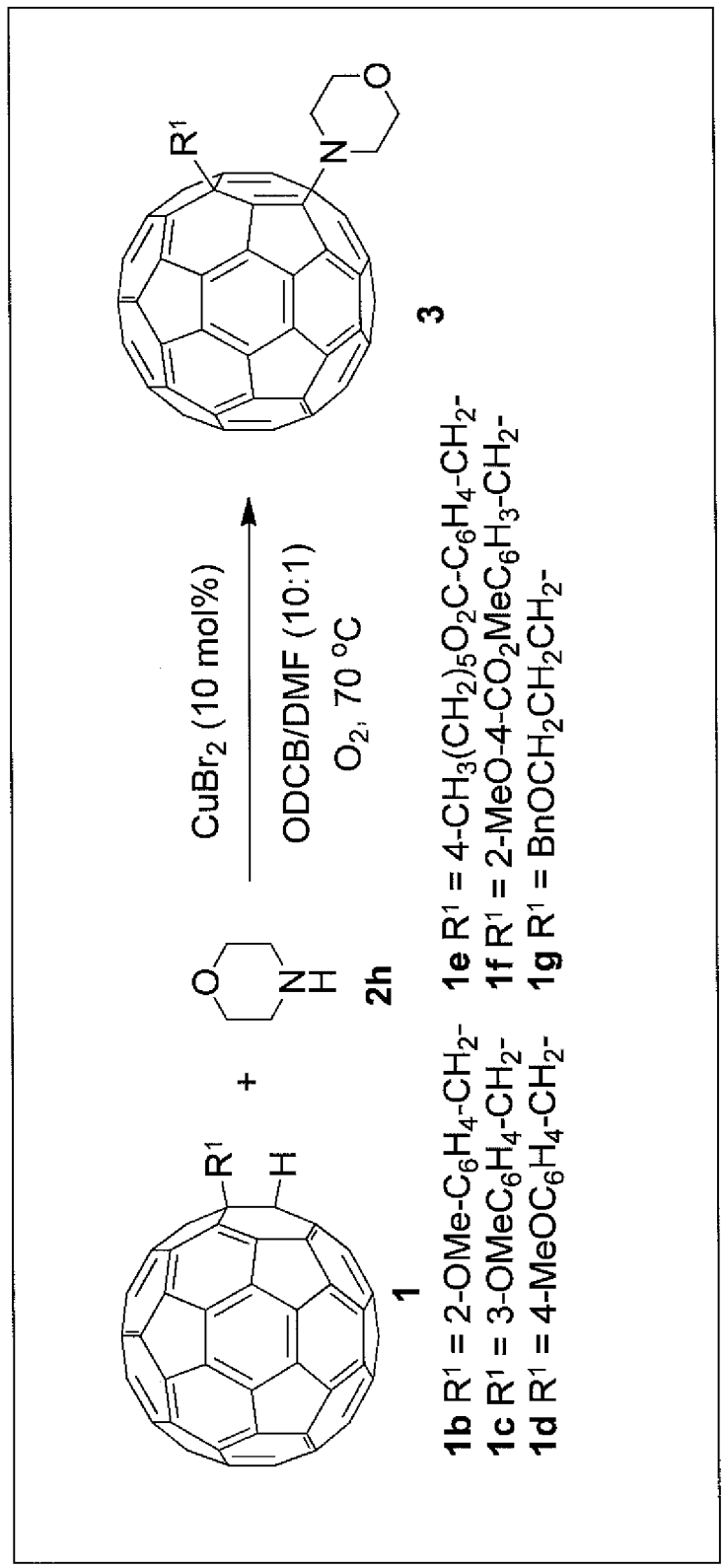
FIG. 3 is a view illustrating an example of an equation between a source fullerene derivative and an amine compound to form a fullerene derivative of the embodiment.

Specifically, examples of the source fullerene derivative 1 are illustrated in FIG. 2. and FIG. 3. A monobenzyl hydrofullerene 1a having a methoxycarbonyl group on 3-position of the benzene ring (see FIG. 2), monobenzyl hydrofullerenes 1b to 1d having a methoxy group on 2-, 3-, and 4-position of the benzene ring, respectively, monobenzyl hydrofullerenes 1e and 1f having a methoxycarbonyl group and both methoxycarbonyl and methoxy groups on the benzene ring, respectively, an alky-substituted hydrofullerene 1g with benzyl-protected alcohol (see FIG. 3) may be exemplified.

(Amine Compound 2)

The amine compound 2 is represented by the above described formula (4). $R^2$ and $R^3$ may be described as above.

Specifically, examples of the amine compound 2 are illustrated in FIG. 2. A variety of acyclic amines, such as dibenzylamine 2a, benzylamine 2b, N-methylaniline 2c, diethylamine 2d and dibutylamine 2e may be exemplified as the amine compound 2. Further, a variety of cyclic amines, such as tetrahydroisoquinoline 2f, thiomorpholine 2g, morpholine 2h, piperidine 2i and 1-phenylpiperazine 2j may be exemplified as the amine compound 2.

(Mechanism)

As will be explained in examples 3-14 and 3-15, according to the present embodiment, it is indicated that the amine compound 2 acts as a base to promote the dimerization of the monobenzyl hydrofullerene 1a in the presence of oxygen. It is also implied that the present amination might proceed through the dimerization of the monobenzyl hydrofullerene 1a to form a single-bonded fullerene dimer 4a (hereinafter, simply referred to as a "dimer 4a", see formula (5), which will be explained later) by the amine base followed by amination of the dimer 4a by the Cu-based catalyst to form the fullerene derivative 3a.

Further, as will be explained in examples 4-1 to 4-4 in addition to examples 3-14 and 3-15, it is indicated that the present amination might proceed through the formation of a fullerene radical intermediate followed by coupling with amine.

On the basis of these results, the reaction mechanism is proposed as illustrated in FIG. 1. FIG. 1 is a view illustrating an example of a scheme of the reaction mechanism of the embodiment.

Deprotonation of an acidic proton in the source fullerene derivative 1 by the amine base 2 forms a fullerenyl monoanion, which oxidizes to a fullerenyl monoradical "A" by an $O_2$-promoted one-electron oxidation (reference (5b)).

In the meanwhile, a coordination "B" of $CuBr_2$ to amine compound 2 forms Cu(II)-amine intermediate "C" along with HBr. The intermediate "C" would be in equilibrium with the amine radical "D" and Cu(I) species. Subsequent intermolecular radical coupling between the fullerene monoradical "A" and the amine radical "D" produces the corresponding fullerene derivative 3. The effect of the DMF polar solvent is assumed to stabilize both two radicals to assist the sufficient radical coupling (reference (5a)).

Finally, $CuBr_2$ is regenerated by oxidation of CuBr under an oxygen atmosphere and in the presence of HBr.

Thus, according to the embodiment, a novel and selective Cu-catalyzed C—H amination of a mono-functionalized hydro-fullerene derivative with various amines is provided. A variety of a monoamine functionalized 1,4-bisadduct fullerene derivatives are obtained in good to high yields.

This methodology provides a valuable and general synthetic tool for the synthesis of various monoamine functionalized 1,4-bisadduct fullerene derivatives that are expected to be useful in electronic device applications.

According to the embodiment, a fullerene derivative in which an alkyl group (or an aralkyl group) and an amino group are provided at 1,4-position of a fullerene core such as $C_{60}$, $C_{70}$, $C_{76}$, $C_{78}$, $C_{82}$, $C_{84}$ or the like is effectively manufactured.

According to the method of manufacturing the fullerene derivative of the embodiment, various fullerene derivatives in which an alkyl group and an amino group are directly bonded to a fullerene core such as $C_{60}$, $C_{70}$, $C_{76}$, $C_{78}$, $C_{82}$, $C_{84}$ or the like are obtained under a moderate condition by applying a specific metal compound (as the catalyst), oxygen and an amine compound to a mono-functionalized hydro-fullerene derivative.

Further, the fullerene derivative 3 represented by the formula (1) is made to have a high solubility to various solvents due to the introduction of the alkyl group (or the aralkyl group) and the amino group and the degree of solubility can also be easily controlled. Thus, the fullerene derivative according to the embodiment can be used as an intermediate for various reactions. Further, the fullerene derivative may be easily formed into a film by coating so that it is possible to manufacture a diode such as an organic thin film solar cell or the like using the film.

The fullerene derivative of the embodiment may be used as new functional materials for electronic components, drugs, cosmetics or the like. In particular, as the number of substituent groups is two, the fullerene derivative of the embodiment is adaptable for a diode such as an organic thin film solar cell or the like.

The fullerene derivative of the embodiment may be used as a material of an organic thin film solar cell.

Figure 4:
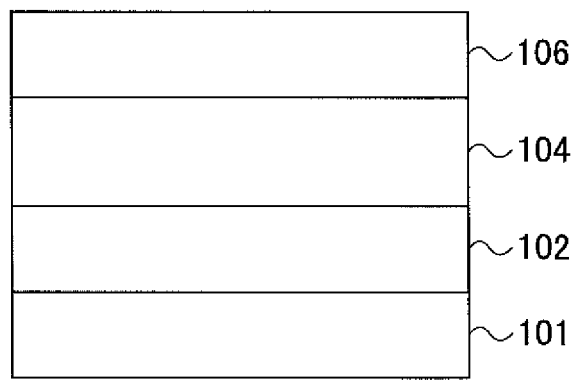
FIG. 4 is a cross-sectional view illustrating an example of a structure of a photoelectric converter.

FIG. 4 is a cross-sectional view illustrating an example of a structure of a photoelectric converter 100, which is an example of a solar cell, of the embodiment. The photoelectric converter 100 includes a substrate 101, a first electrode 102, an active layer 104, and a second electrode 106. At least one of the first electrode 102 and the second electrode 106 is a transparent electrode. The active layer 104 includes at least the fullerene derivative of the embodiment, which is an electron acceptor, and an electron donor compound, and is provided between the first electrode 102 and the second electrode 106.

Materials for the first electrode 102 and the second electrode 106 are not limited as long as having electrical conductivity. However, for example, it is preferable to use a combination of a material having a high work function such as ITO, tin oxide, zinc oxide, Au, Co, Ni, Pt or the like, and a material such as Al, Ag, Li, In, Ca, Mg, LiF or the like for the first electrode 102 and the second electrode 106. In particular, for the transparent electrode, ITO, tin oxide, zinc oxide or the like may be used. A method of manufacturing the electrodes and the thickness of the electrode may be appropriately selected based on a known technology.

For the electron donor compound, any compounds known as an electron donor compound may be used. For example, a conjugated polymer compound, a porphyrin compound, a phthalocyanine compound or the like may be used as the electron donor compound. As the conjugated polymer compound, for example, polythiophene, polypyrrole, polyaniline, polyfuran, polypyridine, polycarbazole, polyphenylene vinylene or the like may be used.

For the electron acceptor compound, the fullerene derivative of the embodiment may be used. Further, another electron acceptor compound may be used in addition to the fullerene derivative of the embodiment. The other electron acceptor compound may be another fullerene derivative, a quinolinol derivative metal complex such as a 8-hydroxyquinoline aluminum, a condensed ring tetracarboxylic diimide such as naphthalene tetracarboxylic diimide, perylene tetracarboxylic diimide or the like, a terpyridine metal complex, a tropolone metal complex, a flavonol metal complex, a perinone derivative, a benzimidazole derivative, a benzoxazole derivative, a benzothiazole derivative, an oxadiazole derivative, a thiadiazole derivative, a triazole derivative, an aldazine derivative, a bisstyryl derivative, a pyrazine derivative, a phenanthroline derivative, a quinoxaline derivative, a benzoquinoline derivative, a bipyridine derivative, a perfluorinated compound of condensed polycyclic aromatic ring such as anthracene, pyrene, naphthacene, pentacene or the like, single-walled carbon nano-tube, an inorganic semiconductor such as titanium dioxide or the like, or the like may be used.

The electron acceptor compound including the fullerene derivative of the embodiment, and the electron donor compound may form a mixed layer or a stacked layer structure in which a layer including the electron acceptor compound and a layer including the electron donor compound are stacked.

When the mixed layer is provided as an active layer 104, the mixed layer is not limited as long as it includes the electron donor compound and the electron acceptor compound. For the electron donor compound and the electron acceptor compound, a single kind of compound may be used, or two or more kinds of compounds of an arbitral combination and ratio may be used, respectively. Further, the mixed layer may include another compound that does not function as an electron donor or an electron acceptor. The thickness of the mixed layer is not specifically limited, but may be 0.1 to 5000 nm, preferably, 1 to 1000 nm, and more preferably 20 to 500 nm.

When the stacked layer structure is provided as an active layer 104, each of the layers is not limited as long as that includes the electron donor compound or the electron acceptor compound. For the electron donor compound and the electron acceptor compound, a single kind of compound may be used, or two or more kinds of compounds of an arbitral combination and ratio may be used, respectively. Further, the stacked layer structure may include another layer including another compound that does not function as an electron donor or an electron acceptor. The thickness of each of the layers is not specifically limited, but may be 0.05 to 2500 nm, preferably 0.5 to 500 nm, and more preferably, 10 to 250 nm. The thickness of the layers may be the same or different.

A method of manufacturing the active layer is not specifically limited, but for example, the active layer may be formed by a wet process such as spin-coating, ink-jet printing, roll-to-roll printing or the like, a dry process such as vapor deposition or the like, or a combination thereof.

EXAMPLES

Examples will be illustrated below for describing the present invention in more detail, but the present invention is not limited to these.

In the following, "Me" represents $CH_3$—, "Et" represents $C_2H_5$—, "Bu" represents $C_4H_9$—, "Bn" represents a benzene ring, "Ph" represents an phenyl group, "Ac" represents $CH_3CO$—, and "Tf" represents $CF_3SO_2$—.

(General Information)

The structures of products were determined by using $^1H$ NMR, $^{13}C$ NMR, high resolution mass spectra (HRMS) and UV-vis spectra.

$^1H$ NMR and $^{13}C$ NMR spectra were recorded on JEOL JMTC-270/54/SS (JASTEC, 400 MHz) spectrometers. $^1H$ NMR spectra are reported as follows: chemical shift in ppm ($\delta$) relative to the chemical shift of $CDCl_3$ at 7.26 ppm, integration, multiplicities (s=singlet, d=doublet, t=triplet, q=quartet, m=multiplet and br=broadened), and coupling constants (Hz). $^{13}C$ NMR spectra are reported in ppm ($\delta$) relative to the central line of triplet for $CDCl_3$ at 77 ppm.

High-resolution mass spectra were obtained on a BRUKER APEXIII spectrometer.

Preparative recycling HPLC (high-performance liquid chromatography) was used with a LC-2000 Plus instrument equipped with a Buckyprep column (4.6 mm×250 mm, nakarai Tesque). HPLC analysis was performed using toluene as an elution at 0.6 ml/min flow rate, whereby detection was at 320 nm at 16° C. Column chromatography was carried out employing silica gel 60 N (spherical, neutral, 40 to 100 m, KANTO Chemical Co.).

Analytical thin-layer chromatography (TLC) was performed on 0.2 mm precoated plate Kieselgel 60 F254 (Merk).

(Materials)

Anhydrous 1,2-dichlorobenzene (Aldrich), toluene, carbon disulfide, DMF (WAKO), Cu-based catalysts (Aldrich), $C_{60}$ (Aldrich), and amines (Aldrich) were purchased and used as received.

Mono-functionalized hydro-fullerene derivatives 1a to 1g were prepared following the references (7) and (3b).

The dimer 4a was prepared following the reference (5a).

Examples 1-1 to 1-10

In example 1-1, the monobenzyl hydrofullerene 1a as described above was used as the source fullerene derivative 1, dibenzylamine 2a was used as the amine compound 2, and $CuBr_2$ was used as the catalyst (see FIG. 2).

To a mixture of 1,2-dichlorobenzene (ODCB) (14 mL) and N,N-dimethylformamide (DMF) (1.4 mL), a solution of the monobenzyl hydrofullerene 1a (87 mg, 0.1 mmol), $CuBr_2$ (0.01 mmol, 2.2 mg) and dibenzylamine 2a (0.2 mmol, 38 µL) was added under an oxygen atmosphere (ballon) at room temperature. The reaction mixture was heated at 70° C. for 18 h.

The reaction was monitored by TLC and HPLC analysis, and the reaction mixture was purified directly through a silica gel chromatography using toluene as an eluent to isolate the corresponding fullerene derivative 3. The obtained product was washed by methanol and dried, affording the fullerene derivative 3a in 71% yield as a dark brown solid (75.6 mg).

Further, under optimized conditions, the scope of $CuBr_2$-catalyzed amination of the monobenzyl hydrofullerene 1a with various amines was further examined.

Similar to example 1-1, the monobenzyl hydrofullerene 1a was used as the source fullerene derivative 1 and $CuBr_2$ was used as the catalyst while the kinds of amine compound 2 were varied as illustrated in FIG. 2 and Table 1.

The reactions were similarly performed as example 1-1. Specifically, reaction conditions were: 1a (0.1 mmol), 2 (2b to 2j) (0.2 mmol), $CuBr_2$ (10 mol %) and ODCB/DMF (10:1, 10 ml), oxygen ballon, 70° C.

Yields of the isolated products, obtained similarly as example 1-1, are illustrated in Table 1. The yields of the corresponding fullerene derivatives 3b to 3e were 54 to 64%. Further, yields of the corresponding fullerene derivatives 3f to 3j were increased, and in particular, the yield of 3j was up to 96% by using 2j.

In some cases, a small amount of the dimer 4a remained and the HPLC analysis did not show any amine multiadducts. The yields of the dimers 4a are determined by HPLC by using $C_{70}$ as an internal standard.

It should be mentioned that the formed fullerene derivative 3 showed high solubility in chloroform, toluene, and ODCB.

TABLE 1

| EXAMPLE | 2 | TIME (h) | 3 | YIELD (%) | 4a (%) |
|---|---|---|---|---|---|
| 1-2 | 2b | 16 | 3b | 64 | 7 |
| 1-3 | 2c | 20 | 3c | 54 | 7 |
| 1-4 | 2d | 16 | 3d | 64 | 6 |
| 1-5 | 2e | 29 | 3e | 61 | 10 |
| 1-6 | 2f | 36 | 3f | 73 | 10 |
| 1-7 | 2g | 55 | 3g | 70 | 9 |
| 1-8 | 2h | 12 | 3h | 86 | 6 |
| 1-9 | 2i | 13 | 3i | 85 | 0 |
| 1-10 | 2j | 17 | 3j | 96 | 0 |

Examples 2-1 to 2-6

The reaction was further examined by using various source fullerene derivatives 1 and morpholine 2h under the standard conditions (FIG. 3 and Table 2).

The reactions were similarly performed as example 1-1. Specifically, reaction conditions were: 1 (1b to 1g) (0.1 mmol), 2h (0.2 mmol), $CuBr_2$ (10 mol %) and ODCB/DMF (10:1, 10 ml), oxygen ballon, 70° C.

Yields of the isolated products, obtained similarly as example 1-1, are illustrated in Table 2. The yields of the corresponding fullerene derivatives 3k to 3m were in good yields. The yields of the corresponding fullerene derivatives 3n and 3o were also tolerated, in 72% and 71% yields, respectively. The yield of the corresponding fullerene derivative 3p obtained under a longer reaction time was in 73%.

It was noted that, in examples 2-3, 2-5 and 2-6, a small amount of $C_{60}$ was formed probably by the elimination of fullerene anions or monoradicals as illustrated in the scheme of the reaction mechanism in FIG. 1. $C_{60}$ were obtained in 16% yield, 6% yield and 9% yield, respectively.

TABLE 2

| EXAMPLE | 1 | TIME (h) | 3 | YIELD (%) |
|---|---|---|---|---|
| 2-1 | 1b | 13 | 3k | 58 |
| 2-2 | 1c | 13 | 3l | 74 |
| 2-3 | 1d | 24 | 3m | 41 |
| 2-4 | 1e | 13 | 3n | 72 |
| 2-5 | 1f | 13 | 3o | 71 |
| 2-6 | 1g | 42 | 3p | 73 |

(Analytic Data of Fullerene Derivatives 3)
(UV-Vis Spectra)

Table S1 illustrates UV-vis absorption of the fullerene derivatives 3a to 3p.

The UV-vis absorption spectra of the fullerene derivatives 3a to 3p exhibit a characteristic broad absorption band around 450 nm, which further supports the 1,4-bisadduct structure of 3 (references (2a) to (4)).

The low symmetry of the fullerene derivatives 3a to 3p showed an increased absorption in the visible region compared to [6,6]-phenyl-$C_{61}$-butyric acid methyl ester ($PC_{61}bM$) which is a well-used benchmark acceptor in bulk hetero-junction solar cells (reference (1)), for example, the extinction coefficient of the fullerene derivatives 3a and 3i are 7000 $mol^{-1}$ $cm^{-1}$ at 444 nm and 447 nm, respectively, which are approximately 2.5 times larger than that of $PC_{61}bM$ (2800 $mol^{-1}$ $cm^{-1}$ at 431 nm) (Table S1).

TABLE S1

| COMPOUND | $\lambda_{max}$/nm ($\epsilon$ $mol^{-1}cm^{-1}$) |
|---|---|
| 3a | 259, 327, 447 (7000) |
| 3d | 259, 327, 443 (6400) |
| 3f | 258, 327, 445 (6500) |
| 3h | 258, 325, 445 (5300) |
| 3i | 260, 328, 444 (7000) |
| 3j | 258, 329, 446 (6000) |
| 3k | 259, 328, 443 (6200) |
| 3l | 259, 328, 446 (6000) |
| 3m | 259, 327, 446 (5800) |
| 3o | 258, 329, 446 (6300) |
| 3p | 258, 328, 452 (6500) |
| $PC_{61b}M$ | 260, 329, 431 (2800) |

(CV)

Table S2 illustrates electrochemical cyclic voltammetry (CV) in ODCB of the fullerene derivatives 3a, 3d, 3f and 3h to 3p. The LUMO energy levels of the fullerene derivative 3 were estimated by the electrochemical cyclic voltammetry (CV) in ODCB.

The fullerene derivatives 3g, 3h and 3j having thiomorpholine, morpholine or 1-phenylpiperazine group on $C_{60}$ core exhibit the LUMO energy levels of −3.67 eV, −3.66 eV, and 3.71 eV respectively, while the fullerene derivatives 3a and 3e having dibenzylamine or dibutylamine substituent group showed slightly higher LUMOs of −3.64 eV and −3.63 eV, respectively. It was noted that the LUMO energy levels of these new fullerene derivatives 3 are much lower than that of $PC_{61}bM$ (−3.60 eV) and 1,4-diarylfullerenes; the latters have been reported to show higher LUMO energy levels than that of $PC_{61}bM$ (reference (2b)). These results indicated that fullerene derivatives having amine addends decease the LUMO energies and demonstrated that LUMO energies of the new monoamine functionalized 1,4-bisadduct fullerene derivatives can be easily tuned by the amine species on $C_{60}$ core.

TABLE S2

| COMPOUND | $E_{1/2}^1$/V | $E_{1/2}^2$/V | $E_{1/2}^3$/V | LUMO/eV |
|---|---|---|---|---|
| 3a | −1.155 | −1.65 | −2.11 | −3.645 |
| 3e | −1.175 | −1.65 | −2.14 | −3.625 |
| 3g | −1.125 | −1.645 | −2.11 | −3.675 |
| 3h | −1.15 | −1.64 | −2.11 | −3.65 |
| 3j | −1.09 | −1.565 | −2.0 | −3.71 |
| $PC_{61}bM$ | −1.205 | −1.595 | −2.11 | −3.595 |

$^1$H NMR, $^{13}$C NMR and HRMS (3a) 1-(Dibenzylamino)-4-[3-(methoxycarbonyl)benzyl]-1,4-dihydro[60]fullerene Dark brown solid; soluble solvents: $CHCl_3$, toluene, ODCB; $^1$H NMR (400 MHz, $CDCl_3/CS_2$=1/4) δ 3.88 (3H, s), 4.24 (1H, d, J=12.8 Hz), 4.44 (1H, d, J=12.8 Hz), 4.80 (2H, d, J=14.0 Hz), 4.87 (2H, d, J=14.0 Hz), 7.28 (2H, dd, J=7.6 Hz, 9.6 Hz), 7.36-7.40 (5H, m), 7.49 (1H, d, J=7.2 Hz), 7.64 (4H, d, J=6.8 Hz), 7.96 (2H, d, J=7.6 Hz), 8.17 (1H, s); $^{13}$C NMR (100 MHz, CDCl$_3$/CS$_2$=1/4) δ 47.31, 51.39, 55.64, 59.31, 73.34, 127.07, 127.77, 128.09, 128.29, 129.05, 130, 131.21, 134.48, 135.61, 138.59, 139.61, 142.02, 142.15, 142.34, 142.41, 142.63, 142.81, 142.93, 143.39, 143.5, 143.65, 143.88, 144.11, 144.29, 144.62; HRMS (ESI, positive) calculated for C$_{83}$H$_{23}$NO$_2$Na [M+Na]$^+$: 1088.1621. found 1088.1621.

(3b) 1-(Benzylamino)-4-[3-(methoxycarbonyl)benzyl]-1,4-dihydro[60]fullerene

Dark brown solid; $^1$H NMR (400 MHz, CDCl$_3$/CS$_2$=1/4) δ 3.93 (3H, s), 4.35 (1H, d, J=12.8), 4.44 (1H, d, J=12.8), 4.51 (2H, s), 7.3-7.46 (6H, m), 7.61 (1H, d, J=8.0), 7.82 (1H, d, J=7.6), 8.27 (1H, s); $^{13}$C NMR (100 MHz, CDCl$_3$/CS$_2$=1/4) δ 48.04, 49.86, 51.58, 59.39, 68.17, 113.39, 126.19, 126.9, 127.73, 128.01, 128.12, 128.92, 130.2, 131.37, 134.62, 135.93, 137.7, 138.77, 139.09, 140.34, 142.05, 142.22, 142.4, 142.57, 142.63, 142.86, 142.89, 143.14, 143.55, 143.72, 143.80, 143.89, 144.04, 144.75, 145.02, 146.32, 146.49, 146.63, 147.32, 147.45, 148.13, 148.34, 150.43, 151.2, 152.8, 165.17; HRMS (ESI, positive) calculated for C$_{76}$H$_{17}$NO$_2$Na [M+Na]$^+$: 998.1152. found 998.1152.

(3c) 1-(N-Methylaniline)-4-[3-(methoxycarbonyl)benzyl]-1,2-dihydro[60]fullerene Dark brown solid; soluble solvents: toluene, ODCB, low in CHCl$_3$; $^1$H NMR (400 MHz, CDCl$_3$/CS$_2$=1/4) δ 3.56 (1H, d, J=12.8 Hz), 3.61 (1H, d, J=12.8 Hz), 3.81 (3H, s), 3.92 (3H, s), 7.27 (1H, dd, J=7.2, 7.6 Hz), 7.41 (1H, dd, J=7.2, 8.0 Hz), 7.54 (1H, dd, J=7.6, 8.4 Hz), 7.58 (1H, d, J=7.6 Hz), 7.73 (1H, d, J=8.4 Hz), 7.93 (1H, d, J=7.6 Hz), 8.06 (1H, s); $^{13}$C NMR (100 MHz, CDCl$_3$/CS$_2$=1/4) δ 38.93, 47.2, 51.45, 59.16, 73.73, 125.52, 127.11, 127.74, 128.12, 128.58, 129.85, 131.51, 134.45, 135.6, 137.48, 138.04, 138.66, 138.71, 140.08, 140.62, 141.64, 141.73, 142.09, 142.12, 142.2, 142.32, 142.37, 142.52, 142.61, 142.7, 142.77, 142.81, 142.84, 143.01, 143.5, 143.53, 143.55, 143.59, 143.66, 143.7, 143.73, 143.76, 143.82, 143.89, 144.07, 144.37, 144.57, 144.79, 144.94, 145.13, 145.22, 146.02, 146.33, 146.44, 146.54, 146.56, 146.59, 147.3, 147.34, 148.02, 148.35, 148.53, 148.68, 149.93, 151.87, 152.52, 165.3; HRMS (ESI, positive) calculated for C$_{76}$H$_{17}$NO$_2$Na [M+Na]$^+$: 998.1152. found 998.1151.

(3d) 1-(Diethylamino)-4-[3-(methoxycarbonyl)benzyl]-1,4-dihydro[60]fullerene Dark brown solid; soluble solvents: toluene, ODCB, low in CHCl$_3$; $^1$H NMR (400 MHz, CDCl$_3$/CS$_2$=1/4) δ 1.6 (3H, t, J=7.2 Hz), 3.71-3.86 (4H, m), 3.91 (3H, s), 4.35 (1H, d, J=12.8 Hz), 4.52 (1H, d, J=12.8 Hz), 7.47 (1H, dd, J=7.6 Hz), 7.77 (1H, d, J=8.0 Hz), 7.99 (1H, d, J=8.0 Hz), 8.21 (1H, s); $^{13}$C NMR (100 MHz, CDCl$_3$/CS$_2$=1/4) δ 15.81, 44.71, 48.01, 51.45, 59.42, 73.32, 127.97, 128.29, 130.04, 131.35, 134.33, 135.77, 138.57, 139.28, 140.18, 141.99, 142.13, 142.37, 142.43, 142.79, 142.87, 142.98, 143.16, 143.22, 143.5, 143.52, 143.78, 143.85, 143.99, 144.13, 144.2, 145.03, 145.12, 145.19, 146.26, 146.31, 146.40, 146.47, 146.49, 146.58, 146.62, 147.32, 148.04, 148.3, 151.78; HRMS (ESI, positive) calculated for C$_{73}$H$_{19}$NO$_2$Na [M+Na]$^+$: 964.1308. found 964.1309.

(3e) 1-(Dibutylamino)-4-[3-(methoxycarbonyl)benzyl]-1,4-dihydro[60]fullerene Dark brown solid; $^1$H NMR (400 MHz, CDCl$_3$/CS$_2$=1/4) δ 1.12-1.17 (6H, m), 1.65-1.72 (3H, m), 1.95-2.01 (4H, m), 3.64-3.73 (4H, m), 3.90 (3H, s), 4.33 (1H, d, J=12.8 Hz), 4.51 (1H, d, J=12.8 Hz), 7.46 (1H, dd, J=8.0 Hz), 7.76 (1H, d, J=7.6 Hz), 7.99 (1H, d, J=8.4 Hz), 8.2 (1H, s); $^{13}$C NMR (100 MHz, CDCl$_3$/CS$_2$=1/4) δ 14.49, 21.15, 32.68, 48.04, 51.29, 51.39, 59.42, 73.5, 127.89, 128.32, 130.05, 131.25, 134.34, 135.69, 137.72, 138.72, 139.32, 140.37, 141.78, 141.9, 142.12, 142.43, 142.6, 142.64, 142.78, 143.12, 143.41, 143.48, 143.77, 143.89, 144.13, 144.22, 144.27, 144.7, 145.05, 145.18, 146.26, 146.31, 146.41, 146.46, 146.48, 146.56, 146.6, 147.08, 147.33, 148.3, 148.85, 149.24, 151.8; HRMS (ESI, positive) calculated for C$_{77}$H$_{27}$NO$_2$Na [M+Na]$^+$: 1020.1934. found 1020.1936.

(3f) 1-(1,2,3,4-Tetrahydroisoquinoline)-4-[3-(methoxycarbonyl)benzyl]-1,4-dihydro[60]fullerene Dark brown solid; $^1$H NMR (400 MHz, CDCl$_3$/CS$_2$=1/4) δ 3.23 (2H, t, J=6.0 Hz), 3.89-3.94 (4H, m), 3.99-4.05 (1H, m), 4.45 (1H, d, J=13.2 Hz), 4.52 (1H, d, J=13.2 Hz), 4.89 (2H, dd, J=14.8, 14.8 Hz), 7.23-7.32 (4H, m), 7.42 (1H, dd, J=7.6, 7.6 Hz), 7.80 (2H, d, J=7.6 Hz), 8.22 (1H, s); $^{13}$C NMR (100 MHz, CDCl$_3$/CS$_2$=1/4) δ 30.14, 46.81, 48.19, 51.33, 51.95, 59.61, 73.41, 125.65, 126.16, 126.44, 127.84, 128.29, 128.48, 129.91, 131.27, 133.74, 134.1, 134.32, 135.56, 137.54, 139.66, 141.57, 141.93, 142.15, 142.45, 142.62, 142.72, 142.83, 142.86, 143.46, 143.61, 143.62, 143.72, 143.76, 143.82, 143.88, 143.9, 144.07, 144.24, 144.64, 144.84, 145.02, 146.25, 146.44, 146.59, 146.71, 147.37, 148.03, 148.33, 149.27, 151.11, 152, 154.82, 165.08, HRMS (ESI, positive) calculated for C$_{78}$H$_{19}$NO$_2$Na [M+Na]$^+$: 1024.1308. found 1024.1311.

(3g) 1-(Thiomorpholino)-4-[3-(methoxycarbonyl)benzyl]-1,4-dihydro[60]fullerene Dark brown solid; $^1$H NMR (400 MHz, CDCl$_3$/CS$_2$=1/4) δ 3.07 (4H, t, J=5.2 Hz), 3.92 (3H, s), 4.01-4.11 (4H, m), 4.36 (1H, d, J=13.2 Hz), 4.51 (1H, d, J=13.2 Hz), 7.49 (1H, dd, J=7.6, 7.6 Hz), 7.78 (1H, d, J=7.6 Hz), 8.01 (1H, d, J=8.0 Hz), 8.19 (1H, s); $^{13}$C NMR (100 MHz, CDCl$_3$/CS$_2$=1/4) δ 29.21, 48.23, 51.53, 51.69, 59.31, 74.27, 29.53, 128.06, 128.39, 130.14, 131.38, 134.38, 135.68, 137.49, 138.25, 138.86, 139.43, 140.26, 140.50, 141.59, 141.82, 141.95, 142.12, 142.19, 142.37, 142.45, 142.48, 142.53, 142.67, 142.73, 142.9, 143.14, 143.47, 143.54, 143.57, 143.62, 143.66, 143.71, 143.8, 143.94, 144.07, 144.27, 144.67, 144.79, 145.05, 145.17, 145.26, 146.23, 146.29, 146.38, 146.5, 146.58, 146.63, 146.75, 147.29, 147.61, 147.76, 148.07, 148.39, 149.71, 151.23, 152.14, 154.27, 165.28; HRMS (ESI, positive) calculated for C$_{73}$H$_{17}$NO$_2$SNa [M+Na]$^+$: 994.0872. found 994.0875.

(3h) 1-(Morpholino)-4-[3-(methoxycarbonyl)benzyl]-1,4-dihydro[60]fullerene

Dark brown solid; $^1$H NMR (400 MHz, CDCl$_3$/CS$_2$=1/4) δ 3.68-3.75 (4H, m), 3.92 (3H, s), 4.05 (4H, t, J=4.4 Hz), 4.38 (1H, d, J=13.2 Hz), 4.52 (1H, d, J=13.2 Hz), 7.49 (1H, dd, J=8.0, 7.2 Hz), 7.78 (1H, d, J=7.6 Hz), 8.02 (1H, d, J=8.0 Hz), 8.20 (1H, s); $^{13}$C NMR (100 MHz, CDCl$_3$/CS$_2$=1/4) δ 48.25, 49.9, 51.55, 59.32, 67.01, 73.8, 128.02, 128.44, 130.08, 131.38, 134.48, 135.68, 137.57, 138.16, 138.82, 139.47, 140.25, 140.46, 141.59, 141.8, 141.96, 141.97, 142.08, 142.18, 142.39, 142.42, 142.48, 142.52, 142.65, 142.72, 142.86, 142.89, 142.91, 143.14, 143.49, 143.53, 143.56, 143.63, 143.72, 143.79, 143.81, 143.90, 144.05, 144.27, 144.64, 144.67, 145.05, 145.15, 145.26, 146.28, 146.35, 146.36, 146.49, 146.58, 146.63, 146.68, 147.34, 147.64, 147.67, 148.06, 148.37, 149.69, 151.01, 152.22, 154.36, 165.35; HRMS (ESI, positive) calculated for $C_{73}H_{17}NO_3Na$ [M+Na]$^+$: 978.1101. found 978.1102.

(3i) 1-(Piperidin-1-yl)-4-[3-(methoxycarbonyl)benzyl]-1,4-dihydro[60]fullerene Dark brown solid; $^1$H NMR (400 MHz, CDCl$_3$/CS$_2$=1/4) δ 1.78-1.80 (2H, m), 2.01-2.06 (4H, m), 3.73-3.76 (4H, m), 3.91 (3H, s), 4.36 (1H, d, J=12.8 Hz), 4.52 (1H, d, J=12.8 Hz), 7.47 (1H, dd, J=8.0, 7.6 Hz), 7.78 (1H, d, J=7.6 Hz), 7.99 (1H, d, J=7.6 Hz), 8.19 (1H, s); $^{13}$C NMR (100 MHz, CDCl$_3$/CS$_2$=1/4) δ 25.14, 26.99, 48.14, 50.77, 51.44, 59.20, 74.35, 127.93, 128.32, 130.00, 131.32, 134.41, 135.74, 137.6, 138.59, 139.33, 140.37, 141.56, 141.72, 141.88, 141.97, 142.11, 142.35, 142.39, 142.62, 142.75, 142.81, 142.86, 142.89, 143.11, 143.34, 143.47, 143.52, 143.55, 143.63, 143.71, 143.73, 143.78, 143.80, 143.85, 144.04, 144.25, 144.61, 144.92, 145.08, 145.14, 146.21, 146.28, 146.44, 146.49, 146.55, 146.78, 147.36, 147.67, 148.00, 148.28, 148.58, 149.23, 151.99, 152.15, 154.29, 165.22. HRMS (ESI, positive) calculated for $C_{76}H_{17}NO_2Na$ [M+Na]$^+$: 976.1308. found 976.1319.

(3j) 1-(4-Phenylpiperazin-1-yl)-4-[3-(methoxycarbonyl)benzyl]-1,4-dihydro[60]fullerene Dark brown solid; $^1$H NMR (400 MHz, CDCl$_3$/CS$_2$=1/4) δ 3.58 (4H, t, J=4.8), 3.83-3.94 (7H, m), 4.37 (1H, d, J=12.8 Hz), 4.52 (1H, d, J=12.8 Hz), 6.85 (1H, dd, J=7.6, 6.8 Hz), 6.99 (2H, d, J=8.0 Hz), 7.24-7.28 (2H, m), 7.47 (1H, dd, J=8.0, 7.6 Hz), 7.78 (1H, d, J=7.6 Hz), 7.98 (1H, d, J=8.0 Hz), 8.20 (1H, s); $^{13}$C NMR (100 MHz, CDCl$_3$/CS$_2$=1/4) δ 48.23, 49.46, 49.71, 51.49, 59.31, 73.62, 115.99, 119.83, 128.02, 128.43, 128.84, 130.08, 131.36, 134.46, 135.65, 137.55, 138.20, 138.81, 139.47, 140.24, 140.48, 141.58, 141.78, 141.93, 141.98, 142.08, 142.16, 142.48, 142.53, 142.56, 142.72, 142.84, 142.87, 142.90, 143.50, 143.54, 143.56, 143.61, 143.7, 143.71, 143.79, 143.80, 143.90, 144.26, 144.63, 144.73, 145.04, 145.13, 145.23, 146.26, 146.35, 146.48, 146.60, 146.71, 147.35, 147.64, 147.90, 148.35, 149.66, 150.63, 152.19, 165.27; HRMS (ESI, positive) calculated for $C_{79}H_{22}N_2O_2Na$ [M+Na]$^+$: 1053.1574. found 1053.1578.

(3k) 1-(Morpholino)-4-(2-methoxybenzyl)-1,4-dihydro[60]fullerene

Dark brown solid; soluble solvents: CHCl$_3$, toluene, ODCB; $^1$H NMR (400 MHz, CDCl$_3$/CS$_2$=1/4) δ 3.71-3.83 (2H, m), 3.85 (3H, s), 4.08 (3H, t, J=4.8 Hz), 4.37 (1H, d, J=12.8 Hz), 4.51 (1H, d, J=12.8 Hz), 6.93 (1H, d, J=8.0 Hz), 6.97 (1H, dd, J=7.6, 7.2 Hz), 7.31 (1H, dd, J=9.2, 8.4 Hz), 7.42 (1H, d, J=7.2 Hz); $^{13}$C NMR (100 MHz, CDCl$_3$/CS$_2$=1/4) δ 42.17, 50.06, 54.48, 59.45, 67.04, 73.77, 110.56, 120.38, 123.69, 128.69, 132.29, 137.34, 140.01, 140.54, 141.57, 142.03, 142.09, 142.18, 142.31, 142.34, 142.39, 142.7, 142.78, 142.83, 143.13, 143.46, 143.59, 143.72, 143.8, 143.89, 144.31, 144.35, 145.04, 145.19, 146.16, 146.54, 146.55, 146.6, 147.4, 147.83, 147.93, 148.32, 151.62, 153.32, 156.01, 157.42; HRMS (ESI, positive) calculated for $C_{72}H_{17}NO_2Na$ [M+Na]$^+$: 950.1152. found 950.1155.

(3l) 1-(Morpholino)-4-(3-methoxybenzyl)-1,4-dihydro[60]fullerene

Dark brown solid; soluble solvents: CHCl$_3$, toluene, ODCB; $^1$H NMR (400 MHz, CDCl$_3$/CS$_2$=1/4) δ 3.70-3.79 (4H, m), 3.83 (3H, s), 4.09 (4H, t, J=4.8 Hz), 4.28 (1H, d, J=12.8 Hz), 4.44 (1H, d, J=12.8 Hz), 6.86 (1H, d, J=8.4 Hz), 7.05 (1H, s), 7.12 (1H, d, J=7.6 Hz), 7.30 (1H, dd, J=8.0, 8.0 Hz); $^{13}$C NMR (100 MHz, CDCl$_3$/CS$_2$=1/4) δ 48.52, 50.01, 54.45, 59.60, 67.01, 73.75, 111.83, 116.75, 122.76, 128.99, 136.49, 137.46, 138.05, 138.94, 140.18, 141.59, 141.66, 141.97, 141.99, 142.06, 142.15, 142.39, 142.44, 142.69, 142.82, 143.14, 143.57, 143.62, 143.72, 143.75, 143.78, 143.86, 144.04, 144.55, 144.73, 145.02, 145.10, 145.22, 146.22, 146.45, 146.54, 146.58, 147.49, 147.66, 148.00, 148.33, 151.11, 152.66, 154.88, 158.90; HRMS (ESI, positive) calculated for $C_{72}H_{17}NO_2Na$ [M+Na]$^+$: 950.1152. found 950.1154.

(3m) 1-(Morpholino)-4-(4-methoxybenzyl)-1,4-dihydro[60]fullerene

Dark brown solid; soluble solvents: THF, CHCl$_3$, toluene, ODCB; $^1$H NMR (400 MHz) δ 3.68-3.79 (4H, m), 3.83 (3H, s), 4.07 (4H, t, J=4.4 Hz), 4.26 (1H, d, J=12.8 Hz), 4.41 (1H, d, J=12.8 Hz), 6.87 (2H, d, J=8.8 Hz), 7.43 (2H, d, J=8.8 Hz); $^{13}$C NMR (100 MHz, CDCl$_3$/CS$_2$=1/4) δ 47.83, 50.07, 54.55, 60.2, 67.11, 73.83, 113.5, 127.01, 131.32, 139.04, 139.4, 140.21, 140.51, 141.65, 141.75, 142.13, 142.22, 142.43, 142.48, 142.68, 142.75, 142.87, 143.57, 143.66, 143.71, 143.77, 143.8, 143.85, 143.88, 143.91, 144.35, 144.58, 144.8, 145.07, 145.26, 146.4, 146.5, 146.6, 146.64, 146.96, 147.57, 147.76, 148.39, 151.25, 155.14, 158.49; HRMS (ESI, positive) calculated for $C_{72}H_{17}NO_2Na$ [M+Na]$^+$: 950.1152. found 950.1153.

(3n) 1-(Morpholino)-4-[4-(pentyloxycarbonyl)benzyl]-1,4-dihydro[60]fullerene Dark brown solid; soluble solvents: CHCl$_3$, toluene, ODCB; $^1$H NMR (400 MHz, CDCl$_3$/CS$_2$=1/4) δ 0.95 (3H, t, J=6.0 Hz), 1.37-1.50 (8H, m), 1.75-1.82 (2H, m), 3.69-3.78 (4H, m), 4.06 (4H, t, J=4.4 Hz), 4.31 (3H, t, J=6.8 Hz), 4.38 (1H, d, J=12.8 Hz), 4.52 (1H, d, J=12.8 Hz), 7.63 (2H, d, J=7.6 Hz), 8.06 (2H, d, J=7.6 Hz); $^{13}$C NMR (100 MHz, CDCl$_3$/CS$_2$=1/4) δ 14.29, 22.95, 25.94, 28.95, 31.67, 48.49, 49.93, 59.24, 64.64, 66.96, 73.78, 129.34, 129.54, 130.24, 138.81, 140.05, 140.26, 140.58, 141.74, 141.96, 142.39, 142.41, 142.48, 142.51, 142.63, 142.86, 142.89, 143.12, 143.47, 143.50, 143.52, 143.73, 143.76, 143.79, 143.90, 144.03, 144.25, 144.62, 145.15, 145.25, 146.27, 146.49, 146.58, 146.63, 147.31, 147.62, 148.36, 152.19, 154.31; HRMS (ESI, positive) calculated for $C_{78}H_{27}NO_3Na$ [M+Na]$^+$: 1048.1883. found 1048.1882.

(3o) 1-(Morpholino)-4-[4-(methoxycarbonyl)-2-methoxylbenzyl]-1,4-dihydro[60]fullerene Dark brown solid; soluble solvents: CHCl$_3$, toluene, ODCB; $^1$H NMR (400 MHz) δ 3.69-3.80 (4H, m), 3.91 (3H, s), 3.92 (3H, s), 4.04 (4H, t, J=4.4 Hz), 4.42 (1H, d, J=12.8 Hz), 4.54 (1H, d, J=12.8 Hz), 7.51 (1H, d, J=7.6 Hz), 7.6 (1H, s), 7.65 (1H, d, J=8.0 Hz); $^{13}$C NMR (100 MHz) δ 42.14, 49.98, 51.51, 54.77, 58.93, 66.95, 73.76, 111.46, 121.74, 129.04, 130.63, 132.05, 137.21, 140.09, 140.51, 141.61, 141.64, 141.98, 142.08, 142.36, 142.42, 142.62, 142.73, 142.77, 142.8, 142.84, 143.35, 143.52, 143.57, 143.65, 143.66, 143.68, 144.3, 144.74, 144.98, 145.07, 145.21, 146.18, 146.3, 146.37, 147.4, 147.75, 147.96, 148.33, 150.4, 151.42, 157.34; HRMS (ESI, positive) calculated for $C_{74}H_{19}NO_4Na$ $[M+Na]^+$: 1008.1206. found 1008.1209.

(3p) 1-(Morpholino)-4-[3-(benzyloxy)propyl]-1,4-dihydro[60]fullerene

Dark purple red solid; soluble solvents: ODCB, low in $CHCl_3$ and toluene; $^1H$ NMR (400 MHz, $CDCl_3/CS_2=1/4$) δ 2.65-2.74 (2H, m), 3.13-3.27 (2H, m) 3.62-3.71 (4H, m), 3.86 (2H, t, J=6.0 Hz), 4.0 (4H, t, J=4.8 Hz), 4.64 (2H, s), 7.26-7.3 (1H, m), 7.32-7.39 (4H, m); $^{13}C$ NMR (100 MHz, $CDCl_3/CS_2=1/4$) δ 27.87, 38.61, 49.77, 58.76, 67.08, 69.85, 72.88, 73.68, 127.06, 127.26, 128.08, 137.42, 137.77, 139.03, 139.44, 140.5, 141.65, 142, 142.12, 142.17, 142.19, 142.40, 142.42, 142.78, 142.82, 142.85, 142.93, 143.17, 143.53, 143.63, 143.77, 143.79, 143.8, 143.87, 144.07, 145.06, 145.1, 145.22, 146.33, 146.4, 146.47, 146.65, 146.85, 147.35, 147.43, 147.79, 148.04, 148.37. 151.34, 153.18, 156.2; UV-vis λmax/nm ($CHCl_3$) 291, 299, 425, 550; HRMS (ESI, positive) calculated for $C_{74}H_{21}NO_2Na$ $[M+Na]^+$: 978.1465. found 978.1466.

Example 3-1 to 3-15

In examples 3-1 to 3-8, various Cu-based catalysts were examined in the reaction of the monobenzyl hydrofullerene 1a and dibenzylamine 2a in a mixture of DMF and ODCB (1:100) at 70° C. under an oxygen atmosphere (Table 3). Specifically, reaction conditions were: 1a (0.1 mmol), 2a (0.2 mmol), Cu-based catalyst (10 mol %), ODCB/DMF (10 mL), oxygen ballon, 70° C. for 18 h.

In example 3-9, THF was used as a co-solvent instead of DMF.

In example 3-10, $CH_3CN$ was used as a co-solvent instead of DMF. A reaction condition was: 1a (0.1 mmol), 2a (0.2 mmol), Cu-based catalyst (10 mol %), ODCB/co-solvent (10 mL), oxygen ballon, 70° C. for 18 h. In example 3-11, ODCB was used as a single solvent. A reaction condition was: 1a (0.1 mmol), 2a (0.2 mmol), Cu-based catalyst (10 mol %), ODCB (10 mL), oxygen ballon, 70° C. for 18 h.

In examples 3-12 to 3-15, the ODCB and DMF ratio was changed from 100:1 to 10:1.

Further, in example 3-13, the reaction was conducted under an air atmosphere. Further in examples 3-14 and 3-15, Cu-based catalyst was not added. Further, in example 3-15, the reaction was conducted under an argon atmosphere. Reaction conditions not particularly mentioned were the same as those of example 3-1.

TABLE 3

| EXAMPLE | CATALYST | SOLVENT (100:1) | 3a (%) | 4a (%) |
|---|---|---|---|---|
| 3-1 | Cu(OAc)$_2$ | ODCB/DMF | 5 | 85 |
| 3-2 | Cu(OTf)$_2$ | ODCB/DMF | 38 | 38 |
| 3-3 | CuCl$_2$ | ODCB/DMF | 37 | 54 |
| 3-4 | CuBr$_2$ | ODCB/DMF | 67 | 20 |
| 3-5 | Cu$_2$O | ODCB/DMF | 40 | 54 |
| 3-6 | CuCl | ODCB/DMF | 34 | 60 |
| 3-7 | CuBr | ODCB/DMF | 58 | 34 |
| 3-8 | CuI | ODCB/DMF | 21 | 70 |
| 3-9 | CuBr$_2$ | ODCB/THF | 40 | 39 |
| 3-10 | CuBr$_2$ | ODCB/CH$_3$CN | 38 | 39 |
| 3-11 | CuBr$_2$ | ODCB | 27 | 13 |
| 3-12 | CuBr$_2$ | ODCB/DMF (10:1) | 75(71) | 0 |
| 3-13 | CuBr$_2$ | ODCB/DMF (10:1) | 43 | 0 |
| 3-14 | none | ODCB/DMF (10:1) | 0 | 90 |
| 3-15 | none | ODCB/DMF (10:1) | 0 | trace |

The yields of the fullerene derivative 3a and the dimer 4a were determined by HPLC analysis using $C_{70}$ as an internal standard. The yield of the fullerene derivative 3a isolated by silica gel chromatography is shown in parentheses. In examples 3-11, 3-13 and 3-15, the monobenzyl hydrofullerene 1a was recovered in 56% yield, 23% yield and 90% yield, respectively.

A certain amount of the fullerene derivative 3a was obtained by using the Cu(II) species such as Cu(OTf)$_2$, CuCl$_2$, and CuBr$_2$ as the Cu-based catalyst (examples 3-2 to 3-5). Among these, CuBr$_2$ obviously increased the yield of the fullerene derivative 3a up to 67% yield together with a 20% yield of the dimer 4a (examples 3-4). Further, Cu(OAc)$_2$ catalyst, which was the most sufficient catalyst for dimerization of the monobenzyl hydrofullerene 1a, exhibited low catalytic activity for producing the fullerene derivative 3a, instead, the dimer 4a was obtained in high yield (example 3-1).

Further, the Cu(I) species, such as Cu$_2$O, CuCl, CuBr, and CuI were also active (examples 3-6 to 3-8) although the yields of the fullerene derivative 3a are lower than that with CuBr$_2$ (example 3-4).

Further, although several other metal catalysts, such as AuBr$_3$, FeCl$_3$, CoBr$_2$, PdCl$_2$, and Mn(OAc)$_3$, were examined, these were totally inactive for the formation of the fullerene derivative 3a and the dimer 4a was obtained in comparable yield.

The use of THF or $CH_3CN$ as a co-solvent instead of DMF (example 3-10) or ODCB as a single solvent (examples 3-11) did not effect on increasing the yield of the fullerene derivative 3a.

Changing the ODCB and DMF ratio from 100:1 to 10:1 increased the yield of the fullerene derivative 3a up to a 71% isolated yield (example 3-12).

43% yield of the fullerene derivative 3a in the reaction under an air atmosphere (example 3-13) indicates that the oxygen atmosphere is indispensable for achieving high chemical yield of 3a.

In the absence of the Cu-based catalyst, the reaction produced the dimer 4a in over 90% yield without formation of the fullerene derivative 3a (example 3-14). However, the similar reaction under an argon atmosphere afforded a trace amount of 4a (example 3-15). These results indicated that the dibenzylamine 2a acts as a base to promote the dimerization of the monobenzyl hydrofullerene 1a in the presence of oxygen. It is also implied that the present amination might proceed through the dimerization of the monobenzyl hydrofullerene 1a to form the dimer 4a by the amine base followed by amination of the dimer 4a by the Cu-based catalyst to form the fullerene derivative 3a.

Example 4-1 to 4-4

The reaction pathway from the dimer 4a to the fullerene derivative 3a was examined (Table 4).

In example 4-1, the dimer 4a was treated with dibenzylamine 2a in the presence of CuBr$_2$ and oxygen. Specifically, a reaction condition was: a mixture of meso and racemic dimer 4a (0.1 mmol), 2a (0.4 mmol), CuBr$_2$ (10 mol %), ODCB/DMF (10:1, 10 mL), oxygen ballon, 70° C. for 18 h. This reaction is represented by the following formula (5).

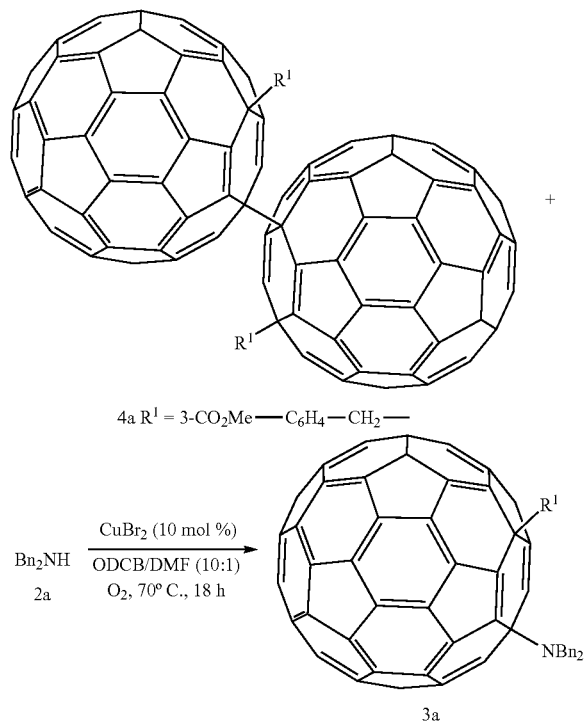

In example 4-2, the reaction was conducted under an argon atmosphere. Further, in example 4-3, Cu-based catalyst was not added. Reaction conditions not particularly mentioned were the same as those of example 4-1.

TABLE 4

| EXAMPLE | CATALYST | OXIDANT | 3a (%) | 4a (%) |
|---------|----------|---------|--------|--------|
| 4-1 | CuBr$_2$ | O$_2$ | 77 | trace |
| 4-2 | CuBr$_2$ | argon | 9 | 80 |
| 4-3 | none | O$_2$ | 0 | 90 |

The yields of the fullerene derivative 3a and the dimer 4a were determined by HPLC analysis using C$_{70}$ as an internal standard.

In example 4-1, the fullerene derivative 3a was obtained in 77% yield, while the reaction produced the fullerene derivative 3a in a very poor yield of 9% under an argon atmosphere (example 4-2). Further, the reaction did not proceed without CuBr$_2$ (example 4-3).

These results clearly indicate that the reaction might be promoted by CuBr$_2$, and the oxygen oxidant is also indispensable for the present transformation.

It was well demonstrated that the single-bonded fullerene dimers dissociate to the stable monoradicals in solution (references (5a), (5b), and (7)). Therefore, the results in examples 3-14, 3-15 and 4-1 to 4-3 indicate that the present amination might proceed through the formation of a fullerene radical intermediate followed by coupling with amine.

Further, Zhang et. al. reported that a fullerene cationic species can be generated from a fullerene radical by using an excess amount of CuCl$_2$ at high temperature (references (2a) and (8)). Murata et. al. demonstrated the fullerene cationic species by the electrophilic addition to allylsilane or benzene to form the corresponding 1,4-bisadducts (reference (4)).

Thus, for example 4-4, to confirm whether the present amination generates the fullerene cation or not, the dimer 4a was treated with anisole under the standard CuBr$_2$-catalyzed reaction condition in the absence of amines. However, the reaction did not produce any anisole-substituted 1,2- or 1,4-bisadducts and the dimer 4a was recovered in over 90% yield. This result indicated that the present amination is unable to generate the fullerene cationic species from the fullerene radical.

REFERENCES (1) Li, C.-Z.; Yip, H.-L.; Jen, A. K.-Y., Functional fullerenes for organic photovoltaics, *J. Mater. Chem.* 2012, 22, 4161.

(2a) Zhang, Y.; Matsuo, Y.; Li. C.-Z.; Tanaka, H.; Nakamura, E., A Scalable Synthesis of Methano[60]fullerene and Congeners by the Oxidative Cyclopropanation Reaction of Silylmethylfullerene, *J. Am. Chem. Soc.* 2011, 133, 8086.

(2b) Varotto, A.; Treat, N. D.; Jo, J.; Shuttle, C. G.; Batara, N. A.; Brunetti, F. G.; Seo, J. H.; Chabinyc, M. L.; Hawker, C. J.; Heeger, A. J.; Wudl, F., 1,4-Fullerene Derivatives: Tuning the Properties of the Electron Transporting Layer in Bulk-Heterojunction Solar Cells, Angew. Chem. *Int. Ed.* 2011, 50, 5166.

(3a) Fukuzumi, S.; Suenobu, T.; Hirasaka, T.; Arakawa, R.; Kadish, K. M., Formation of C$_{60}$ Adducts with Two Different Alkyl Groups via Combination of Electron Transfer and S$_N$2 Reactions, *J. Am. Chem. Soc.* 1998, 120, 9220.

(3b) Matsuo, Y.; Iwashita, A.; Abe, Y.; Li, C. Z.; Matsuo, K.; Hashiguchi, M.; Nakamura, E., Regioselective Synthesis of 1,4-Di(organo) [60]fullerenes through DMF-assisted Monoaddition of Silylmethyl Grignard Reagents and Subsequent Alkylation Reaction, *J. Am. Chem. Soc.* 2008, 130, 15429.

(4) Murata, Y.; Cheng, F.; Kitagawa, T.; Komatsu, K., Generation of Fullerenyl Cation (EtO)$_2$P$^+$(OH) CH$_2$—C$_{60}^+$ from RC$_{60}$—H and from RC$_{60}$—C$_{60}$R (R=CH$_2$P(O)(OEt)$_2$), *J. Am. Chem. Soc.* 2004, 126, 8874.

(5a) Lu, S.; Jin, T.; Kwon, E.; Bao, M.; Yamamoto, Y., Highly Efficient Cu(OAc)$_2$-Catalyzed Dimerization of Monofunctionalized Hydrofullerenes Leading to Single-Bonded [60]Fullerene Dimers, *Angew. Chem. Int. Ed.* 2012, 51, 802.

(5b) Lu, S.; Jin, T.; Bao, M.; Yamamoto, Y., NaOH-Catalyzed Dimerization of Monofunctionalized Hydrofullerenes: Transition-Metal-Free, General, and Efficient Synthesis of Single-Bonded [60]Fullerene Dimers, *Org. Lett.* 2012, 14, 3466.

(6) Hirsch, A.; Li, Q.; Wudl, F., Globe-trotting Hydrogens on the Surface of the Fullerene Compound C$_{60}$H$_6$(N(CH$_2$CH$_2$)$_2$O)$_6$, *Angew. Chem. Int. Ed. Engl.* 1991, 30, 1309.

(7) Lu, S.; Jin, T.; Bao, M.; Yamamoto, Y., Cobalt-Catalyzed Hydroalkylation of [60]Fullerene with Active Alkyl Bromides: Selective Synthesis of Monoalkylated Fullerenes, *J. Am. Chem. Soc.* 2011, 133, 12842.

(8) Zhang, Y.; Matsuo, Y.; Nakamura, E., Regiocontrolled Synthesis of 1,2-Di(organo)fullerenes via Copper-Assisted 1,4-Aryl Migration from Silicon to Carbon, *Org. Lett.* 2011, 13, 6058.

Although a preferred embodiment of the fullerene derivative and the method of manufacturing the fullerene derivative has been specifically illustrated and described, it is to be understood that minor modifications may be made therein without departing from the spirit and scope of the invention as defined by the claims.

The present invention is not limited to the specifically disclosed embodiments, and numerous variations and modifications and modifications may be made without departing from the spirit and scope of the present invention.

What is claimed is:

1. A fullerene derivative represented by the following formula (1):

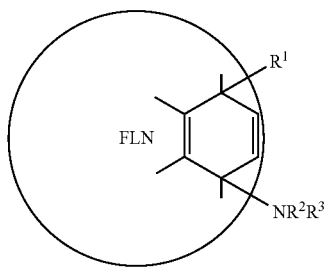

(1)

wherein "FLN" represents a fullerene core selected from a group consisting of fullerene $C_{60}$, fullerene $C_{70}$, fullerene $C_{76}$, fullerene $C_{78}$, fullerene $C_{82}$ and fullerene $C_{84}$;

wherein $R^1$ represents substituted or non-substituted $C_1$-$C_{24}$ alkyl group or substituted or non-substituted $C_7$-$C_{24}$ aralkyl group, the aralkyl group being selected from a group consisting of a benzyl group, a 2-phenylethyl group, a 1-phenylethyl group and a 3-phenylpropyl group, when the alkyl group or the aralkyl group is substituted, the substituent group being selected from a group consisting of a $C_1$-$C_{10}$ hydrocarbon group, a $C_1$-$C_{10}$ alkoxy group, a $C_6$-$C_{12}$ aryloxy group, a $C_1$-$C_{10}$ acyloxy group, a $C_1$-$C_{10}$ oxycarbonyl group, a $C_1$-$C_{10}$ acyl group, a nitro group, an amino group, an amide group, a nitrile group, a silyl group, a phosphine group and a halogen atom;

wherein $R^2$ and $R^3$ independently represent a hydrogen atom or substituted or non-substituted $C_1$-$C_{24}$ hydrocarbon group but excluding a case where both of $R^2$ and $R^3$ are hydrogen atoms, and $R^2$ and $R^3$ may combine together to form a ring, the $C_1$-$C_{24}$ hydrocarbon group being selected from a group consisting of an alkyl group, an aromatic group, and an aralkyl group, the aromatic group being selected from a group consisting of a phenyl group, an indenyl group, a naphthyl group, an anthracenyl group, a phenanthrenyl group, a fluorenyl group and a pyrenyl group, the aralkyl group being selected from a group consisting of a benzyl group, a 2-phenylethyl group, a 1-phenylethyl group and a 3-phenylpropyl group, when the $C_1$-$C_{24}$ hydrocarbon group is substituted, the substituent group being selected from a group consisting of a $C_1$-$C_{10}$ hydrocarbon group, a $C_1$-$C_{10}$ alkoxy group, a $C_6$-$C_{12}$ aryloxy group, a $C_1$-$C_{10}$ acyloxy group, an aldehyde group, a $C_1$-$C_{10}$ oxycarbonyl group, a $C_1$-$C_{10}$ acyl group, a nitro group, an amino group, an amide group, a nitrile group, a silyl group, a phosphine group and a halogen atom.

2. The fullerene derivative according to claim 1, wherein the fullerene core represented by "FLN" is at least one of fullerene C60 and fullerene C70.

3. The fullerene derivative according to claim 1, wherein the fullerene core represented by "FLN" is fullerene C60.

4. The fullerene derivative according to claim 1, wherein $R^1$ is a benzyl group without a substituent group, or with at least one substituent group on a corresponding position of the benzene ring selected from a group consisting of a $C_1$-$C_{10}$ hydrocarbon group, a $C_1$-$C_{10}$ alkoxy group and a $C_1$-$C_{10}$ oxycarbonyl group.

5. The fullerene derivative according to claim 1,
wherein $R^1$ is selected from a group consisting of a benzyl group without a substituent group, or with one or more substituent groups on one or more positions of the benzene ring selected from a group consisting of a $C_1$-$C_{10}$ hydrocarbon group, a $C_1$-$C_{10}$ alkoxy group and a $C_1$-$C_{10}$ oxycarbonyl group.

6. The fullerene derivative according to claim 5,
wherein the $C_1$-$C_{10}$ hydrocarbon group is selected from a group consisting of methyl, ethyl, propyl, butyl, phenyl, naphthyl, indenyl, tolyl, xylyl and benzyl,
wherein the $C_1$-$C_{10}$ alkoxy group is selected from a group consisting of a methoxy group, an ethoxy group, a propoxy group, a butoxy group and a benzyloxy group, and
wherein the $C_1$-$C_{10}$ oxycarbonyl group is selected from a group consisting of a methoxycarbonyl group and a hexyloxycarbonyl group.

7. The fullerene derivative according to claim 5,
wherein $R^1$ is a benzyl group without a substituent group, or with one or more substituent groups on one or more positions of the benzene ring selected from a group including a methoxy group, and a methoxycarbonyl group.

8. The fullerene derivative according to claim 1,
wherein $R^1$ is selected from a group consisting of 2-OMe-$C_6H_4$—$CH_2$—, 3-OMe-$C_6H_4$—$CH_2$—, 4-MeO$C_6H_4$—$CH_2$—, 4-$CH_3(CH_2)_5O_2C$—$C_6H_4$—$CH_2$—, 2-MeO-4-$CO_2MeC_6H_3$—$CH_2$— and BnO$CH_2CH_2CH_2$—, where Me represents $CH_3$— and Bn represents a benzene ring.

9. The fullerene derivative according to claim 1,
wherein $R^2R^3N$— is selected from a group consisting of a methylamino group, an ethylamino group, a n-propylamino group, an isopropylamino group, a n-butylamino group, an isobutylamino group, a n-hexylamino group, a benzylamino group, a phenylamino group, a tolylamino group, a dimethylamino group, a diethylamino group, a di(n-propyl)amino group, a diisopropylamino group, a di(n-butyl)amino group, a diisobutylamino group, a di(n-hexyl)amino group, a dibenzylamino group, a diphenylamino group, a ditolylamino group, a methylphenylamino group, a piperidino group, a morpholino group, a thiomorpholino group and a tetrahydroisoquinolino group.

10. The fullerene derivative according to claim 1,
wherein $R^2R^3N$— is a morpholino group.

11. The fullerene derivative according to claim 1,
wherein $R^2R^3N$— is selected from a group consisting of a dibenzylamino group, a benzylamino group, an N-methylaniline group, a diethylamino group, a dibutylamino group, a tetrahydroisoquinoline group, a thiomorpholino group, a morpholino group, a piperidyl group and an 1-phenylpiperazine group.

* * * * *